(12) United States Patent
Shao et al.

(10) Patent No.: US 10,428,021 B2
(45) Date of Patent: *Oct. 1, 2019

(54) TRIPLE REUPTAKE INHIBITORS AND METHODS OF THEIR USE

(71) Applicant: SUNOVION PHARMACEUTICALS INC., Marlborough, MA (US)

(72) Inventors: Liming Shao, Lincoln, MA (US); Fengjiang Wang, Northborough, MA (US); Scott C. Malcolm, Southborough, MA (US); Michael C. Hewitt, Somerville, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/817,760

(22) Filed: Nov. 20, 2017

(65) Prior Publication Data

US 2018/0148407 A1    May 31, 2018

Related U.S. Application Data

(63) Continuation of application No. 14/850,338, filed on Sep. 10, 2015, now Pat. No. 9,850,204, which is a continuation of application No. 14/062,626, filed on Oct. 24, 2013, now Pat. No. 9,133,117, which is a continuation of application No. 13/139,967, filed on Sep. 2, 2011, now Pat. No. 8,592,608.

(51) Int. Cl.
*A61K 31/4035* (2006.01)
*C07D 209/44* (2006.01)
*C07D 209/08* (2006.01)
*C07D 209/52* (2006.01)

(52) U.S. Cl.
CPC ........ *C07D 209/44* (2013.01); *A61K 31/4035* (2013.01); *C07D 209/08* (2013.01); *C07D 209/52* (2013.01)

(58) Field of Classification Search
None
See application file for complete search history.

(56) References Cited

U.S. PATENT DOCUMENTS

| | | | |
|---|---|---|---|
| 4,544,665 A * | 10/1985 | Epstein | C07D 495/10 514/412 |
| 8,592,608 B2 * | 11/2013 | Shao | C07D 209/08 546/139 |
| 9,133,117 B2 * | 9/2015 | Shao | C07D 209/08 |

OTHER PUBLICATIONS

The English translaiton of the Japanese Office Action, dated Feb. 5, 2019, in the related Japanese Appl. No. 2018-072080.

* cited by examiner

*Primary Examiner* — Samantha L Shterengarts

(57) ABSTRACT

Provided herein are bicyclic compounds and methods of synthesis thereof. The compounds provided herein are useful for the treatment, prevention, and/or management of various neurological disorders. Compounds provided herein inhibit reuptake of endogenous monoamines, such as dopamine, serotonin and norepinephrine (e.g., from the synaptic cleft) and modulate one or more monoamine transporter. Pharmaceutical formulations containing the compounds are also provided.

11 Claims, 3 Drawing Sheets

Top: (3aR,7aS)-3a-(3,4-dichlorophenyl)-2-methyloctahydro-1H-isoindole
Second: (3aS,7aR)-3a-(3,4-dichlorophenyl)-2-methyloctahydro-1H-isoindole
Third: (3aS,6aR)-3a-(3,4-dichlorophenyl)-2-methyloctahydro cyclopenta[c]pyrrole
Fourth: (3aR,6aS)-3a-(3,4-Dichlorophenyl)-2-methyloctahydrocyclopenta[c]pyrrole Top: (3aS,7aR)-3a-(3,4-dichlorophenyl)-2-methyloctahydro-1H-isoindole
Second: (3aR,7aS)-3a-(3,4-dichlorophenyl)-2-methyloctahydro-1H-isoindole
Third: (3aS,6aR)-3a-(3,4-dichlorophenyl)-2-methyloctahydro cyclopenta[c]pyrrole
Fourth: (3aR,6aS)-3a-(3,4-Dichlorophenyl)-2-methyloctahydrocyclopenta[c]pyrrole

TRIPLE REUPTAKE INHIBITORS AND METHODS OF THEIR USE

This application claims priority to and is a continuation of pending U.S. patent application Ser. No. 14/850,338, filed Sep. 10, 2015, which in turn claims priority to and is a continuation of U.S. patent application Ser. No. 14/062,626, filed Oct. 24, 2013, and patented as U.S. Pat. No. 9,133,117, on Sep. 15, 2015; which in turn claims priority to and is a continuation of U.S. patent application Ser. No. 13/139,967, filed Sep. 2, 2011, and patented as U.S. Pat. No. 8,592,608 on Nov. 26, 2013; which in turn claims priority to 371 of International Application Number PCT/US09/68016, filed Dec. 15, 2009, which in turn claims benefit from U.S. Provisional Patent Application Ser. No. 61/138,062, filed Dec. 16, 2008, all of which are hereby incorporated by reference in their entireties.

1. FIELD

Provided herein are compounds useful as triple reuptake inhibitors, compositions comprising the compounds, and methods of their use.

2. BACKGROUND

Monoamine neurotransmitters have been implicated in the body's response to neurological disorders such as pain and depression. Norepinephrine (NE) and serotonin (5-HT) are monoamine neurotransmitters originating in the brain and projecting diffusely throughout the central nervous system. 5-HT and NE are reported to be involved in modulating pain transmission from the spinal cord to the brain and also governing the body's moods and responses to stress.

Depression refers to an abnormal mood or a collection of symptoms that constitute a psychiatric disorder. Symptoms of depression include disturbances in mood and affect (depressed mood, diminished interest and pleasure in activities), bodily function (weight and appetite changes, psychomotor disturbances, sleep disturbances, fatigue, and loss of energy), and cognitive processes (feelings of worthlessness and guilt, concentration difficulties, indecisiveness, thoughts of death or suicide, and possibly delusions/hallucinations). These symptoms vary in intensity, duration and frequency and permit classification of depression into different classes. Other symptoms of major depressive episodes include crying spells, self-pity, hopelessness, irritability, brooding, diminished self-esteem, decreased libido, nihilism, social withdrawal, memory impairment, feelings of inadequacy, and pessimism.

It has been reported that electrical stimulation of certain brain regions releases 5-HT and NE, which are believed to produce an analgesia in both animals and humans. Conversely, it has been reported that depletion of serotonin in the rat results in an enhanced response to pain. There also appears to be synergistic actions between NE and 5-HT in modulating pain sensation. Studies in the rat show that the analgesia from exogenously administered 5-HT can be blocked by depleting NE in the spinal cord.

Common antidepressants increase synaptic availability of biogenic amines by blocking their major means of physiological inactivation, which involves transport or reuptake into nerve terminals. Examples include "dual" action agents that inhibit the reuptake of both NE and 5-HT (e.g., venlafaxine and milnacipram), selective serotonin reuptake inhibitors (SSRIs) (e.g., fluoxetine and sertraline), and norepinephrine reuptake inhibitors (e.g., Reboxetine). A major drawback to all of these agents is the therapeutic lag associated with their use—patients must take the drug for up to 3 weeks to achieve clinically meaningful symptomatic relief. Furthermore, a significant number of patients do not respond to current therapies at all. For example, it is currently estimated that up to thirty percent (30%) of clinically diagnosed cases of depression are resistant to all forms of current drug therapy. Consequently, there is a significant need for effective treatments of various neurological disorders.

3. SUMMARY

Provided herein are compounds of formula (I), or pharmaceutically acceptable salt or solvate thereof:

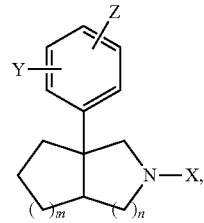

wherein X, Y, Z, m, and n are defined herein elsewhere. The compounds are useful as "triple reuptake inhibitors."

Also provided herein are compositions and dosage forms comprising compounds provided herein. Compositions and dosage forms provided herein may comprise one or more additional active ingredients.

Also provided herein are methods for the treatment, prevention, and/or management of various neurological disorders using the compounds and compositions provided herein. Neurological disorders that may be treated, prevented, and/or managed include, but are not limited to, depression (e.g., major depressive disorder, bipolar disorder), fibromyalgia, pain (e.g., neuropathic pain), sleep apnea, attention deficit disorder (ADD), attention deficit hyperactivity disorder (ADHD), restless leg syndrome, schizophrenia, anxiety, obsessive compulsive disorder, post-traumatic stress disorder, seasonal affective disorder (SAD), premenstrual dysphoria, neurodegenerative diseases (e.g., Parkinson's disease, Alzheimer's disease) and any other neurological disorders described herein elsewhere. In addition, methods for the treatment, prevention, and/or management of obesity or treatment of substance abuse, dependency or addiction, including but not limited to nicotine and cocaine abuse, dependency or addiction are also provided herein.

In another embodiment, provided herein is a method of inhibiting binding of a monoamine transporter ligand to a monoamine transporter, such as serotonin transporter, dopamine transporter and norepinephrine transporter. The method comprises contacting the monoamine transporter and a compound of the invention. In an exemplary embodiment, the monoamine transporter ligand is a monoamine, such as serotonin, dopamine and norepinephrine.

Also provided herein is a method of inhibiting the activity of at least one monoamine transporter, such as serotonin transporter, dopamine transporter and norepinephrine transporter. The method comprises contacting the monoamine transporter and a compound provided herein.

Also provided herein is a method of inhibiting uptake of at least one monoamine, such as serotonin, dopamine and norepinephrine, by a cell. The method comprises contacting the cell with a compound of the invention. In an exemplary embodiment, the cell is a brain cell, such as a neuronal cell or a glial cell.

4. BRIEF DESCRIPTION OF FIGURES

5. DETAILED DESCRIPTION

5.1 Definitions

Figure 1:
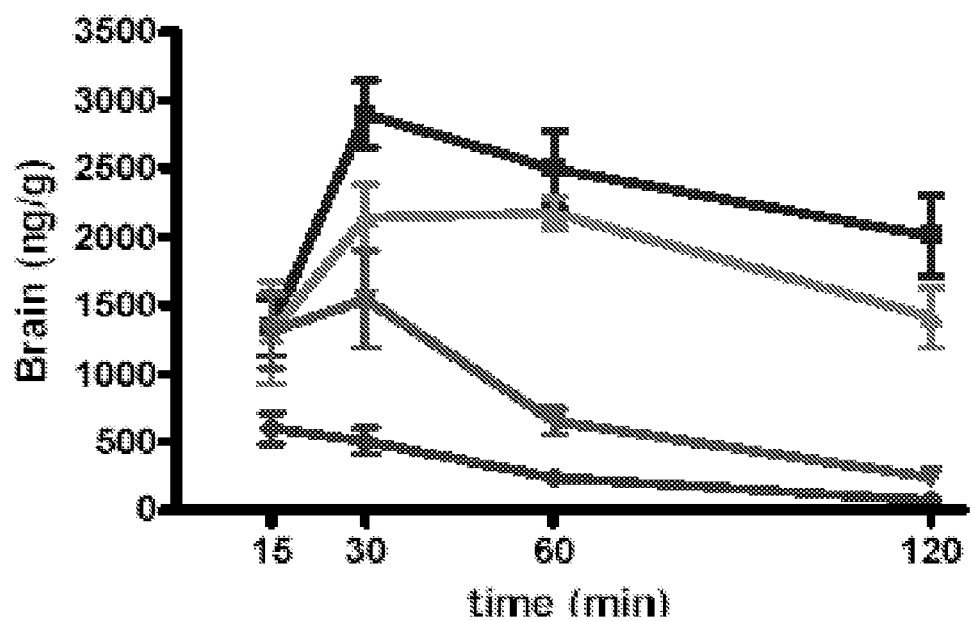
FIG. 1 illustrates the levels of tested compounds in brain following an oral administration at a dose of 10 mg/kg.
Figure 2:
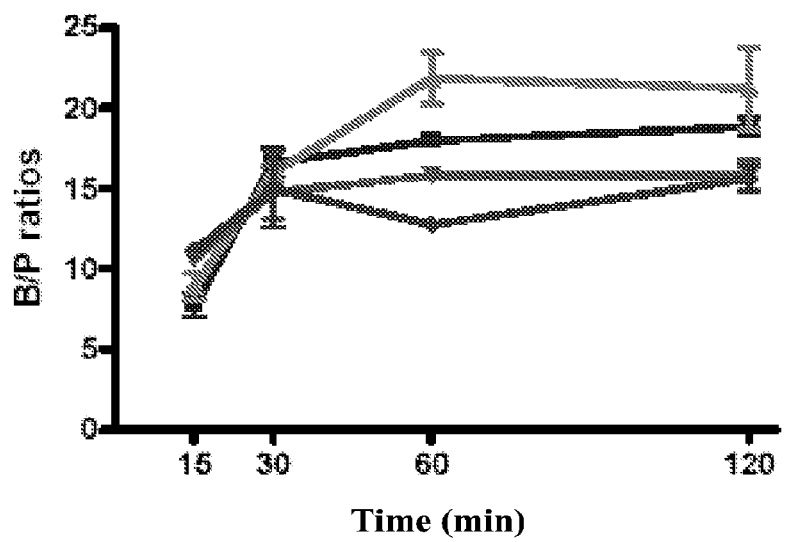
FIG. 2 illustrates the ratio of brain and plasma levels of the tested compounds following an oral administration at a dose of 10 mg/kg.

As used herein, and unless otherwise indicated, the term "alkyl" refers to a linear or branched saturated monovalent hydrocarbon radical, wherein the alkyl may optionally be substituted with one or more substituents. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

As used herein, and unless otherwise specified, the term "alkenyl" refers to a linear or branched monovalent hydrocarbon radical, which contains one or more, in one embodiment, one to five, carbon-carbon double bonds. The alkenyl may be optionally substituted one or more substituents. The term "alkenyl" also encompasses radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

As used herein, and unless otherwise specified, the term "alkynyl" refers to a linear or branched monovalent hydrocarbon radical, which contains one or more, in one embodiment, one to five, carbon-carbon triple bonds. The alkynyl may be optionally substituted one or more substituents. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

As used herein, and unless otherwise specified, the term "cycloalkyl" refers to a cyclic saturated bridged and/or non-bridged monovalent hydrocarbon radical, which may be optionally substituted one or more substituents as described herein. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl.

As used herein, and unless otherwise specified, the terms "heteroalkyl," "heteroalkenyl," and "heteroalkynyl" refer to alkyl, alkenyl, and alkynyl, respectively, wherein one or more carbon atoms are replaced with heteroatoms.

As used herein, and unless otherwise specified, the term "heteroatom" refers to any atom other than carbon or hydrogen. In some embodiments, the term "heteroatom" refers to N, O, S, Si, or P. In other embodiments, the term "heteroatom" refers to N, O, or S.

As used herein, and unless otherwise specified, the term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may also be optionally substituted with one or more substituents.

As used herein, and unless otherwise specified, the term "arylalkyl" or "aralkyl" refers to a monovalent alkyl group substituted with aryl. In certain embodiments, both alkyl and aryl may be optionally substituted with one or more substituents.

As used herein, and unless otherwise specified, the term "pharmaceutically acceptable salts" refers to salts prepared from pharmaceutically acceptable non-toxic acids, including inorganic acids and organic acids. Suitable non-toxic acids include inorganic and organic acids such as, but not limited to, acetic, alginic, anthranilic, benzenesulfonic, benzoic, camphorsulfonic, citric, ethenesulfonic, formic, fumaric, furoic, gluconic, glutamic, glucorcnic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like. In some embodiments, the salt is formed from hydrochloric, hydrobromic, phosphoric, or sulfuric acid. In one embodiment, the salt is formed from hydrochloride salt.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/stereomerically pure and enantiomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stercomerically enriched composition of a compound having one chiral center.

As used herein, and unless otherwise indicated, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise indicated, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing," and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice and the like. In specific embodiments, the subject is a human.

As used herein, and unless otherwise specified, the term "monoamine transporter ligand" refers to any compound, which binds to a monoamine transporter. Ligands include endogenous monoamines, which are the natural ligands for a given monoamine transporter as well as drug molecules and other compounds, such as synthetic molecules known to bind to a particular monoamine transporter. In one example, the ligand includes a radioisotope, such as tritium or is otherwise (e.g., fluorescently) labeled. It is within the abilities of the skilled person to select an appropriate ligand for a given monoamine transporter. For example, known ligands for the dopamine transporter include dopamine and WIN35428, known ligands for the serotonin transporter include 5-hydroxytryptamine (serotonin) and citalopram, and ligands for the norepinephrine transporter include norepinephrine and nisoxetine.

As used herein, and unless otherwise specified, the term "neurological disorder" refers to any condition of the central or peripheral nervous system of a mammal. The term "neurological disorder" includes, but is not limited to, neurodegenerative diseases (e.g., Alzheimer's disease, Parkinson's disease and amyotrophic lateral sclerosis), neuropsychiatric diseases (e.g., schizophrenia and anxieties, such as general anxiety disorder), and affective disorders (e.g., depression and attention deficit disorder). Exemplary neurological disorders include, but are not limited to, MLS (cerebellar ataxia), Huntington's disease, Down syndrome, multi-infarct dementia, status epilecticus, contusive injuries (e.g., spinal cord injury and head injury), viral infection induced neurodegeneration, (e.g., AIDS, encephalopathies), epilepsy, benign forgetfulness, closed head injury, sleep disorders, depression (e.g., bipolar disorder), dementias, movement disorders, psychoses, alcoholism, post-traumatic stress disorder and the like. "Neurological disorder" also includes any condition associated with the disorder. For instance, a method of treating a neurodegenerative disorder includes methods of treating loss of memory and/or loss of cognition associated with a neurodegenerative disorder. An exemplary method would also include treating or preventing loss of neuronal function characteristic of neurodegenerative disorder. "Neurological disorder" also includes any disease or condition that is implicated, at least in part, in monoamine (e.g., norepinephrine) signaling pathways (e.g., cardiovascular disease).

As used herein, and unless otherwise specified, the term "affective disorder" includes depression, attention deficit disorder, attention deficit disorder with hyperactivity, bipolar and manic conditions, and the like. The terms "attention deficit disorder" (ADD) and "attention deficit disorder with hyperactivity" (ADDH), or attention deficit/hyperactivity disorder (AD/HD), are used herein in accordance with the accepted meanings as found in the *Diagnostic and Statistical Manual of Mental Disorders*, 4$^{th}$ Ed., American Psychiatric Association (1997) (DSM-IV™).

As used herein, and unless otherwise specified, the term "depression" includes all forms of depression including, but not limited to, major depressive disorder (MDD), bipolar disorder, seasonal affective disorder (SAD) and dysthymia. "Major depressive disorder" is used herein interchangeably with "unipolar depression" and "major depression." "Depression" may also includes any condition commonly associated with depression, such as all forms of fatigue (e.g., chronic fatigue syndrome) and cognitive deficits.

As used herein, and unless otherwise specified, the terms "obsessive-compulsive disorder," "substance abuse," "premenstrual syndrome," "anxiety," "eating disorders" and "migraine" are used herein in a manner consistent with their accepted meanings in the art. See, e.g., DSM-IV™. For example, the term "eating disorder," as used herein, refers to abnormal compulsions to avoid eating or uncontrollable impulses to consume abnormally large amounts of food. These disorders may affect not only the social well-being, but also the physical well-being of sufferers. Examples of eating disorders include, but are not limited to, anorexia nervosa, bulimia, and binge eating.

As used herein, and unless otherwise specified, the term "pain" refers to an unpleasant sensory and emotional experience. The term "pain," as used herein, refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (see, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia. In addition, The term "pain" includes pain resulting from dysfunction of the nervous system: organic pain states that share clinical features of neuropathic pain and possible common pathophysiology mechanisms, but are not initiated by an identifiable lesion in any part of the nervous system.

The term "somatic pain," as used herein, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

The term "neuropathic pain," as used herein, refers to a heterogeneous group of neurological conditions that result from damage to the nervous system. The term also refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis, and is also encompassed by the term. Other types of pain that are meant to be included in the definition of neuropathic pain include, but are not limited to, pain from neuropathic cancer pain, HIV/AIDS induced pain, phantom limb pain, and complex regional pain syndrome.

The term also encompasses the common clinical features of neuropathic pain including, but not limited to, sensory loss, allodynia (non-noxious stimuli produced pain), hyperalgesia and hyperpathia (delayed perception, summation, and painful aftersensation). Pain is often a combination of nociceptive and neuropathic types, for example, mechanical spinal pain and radiculopathy or myelopathy.

As used herein, and unless otherwise specified, the term "acute pain" refers to the normal, predicted physiological response to a noxious chemical, thermal or mechanical stimulus typically associated with invasive procedures, trauma and disease. It is generally time-limited, and may be viewed as an appropriate response to a stimulus that threatens and/or produces tissue injury. The term also refers to pain which is marked by short duration or sudden onset.

As used herein, and unless otherwise specified, the term "chronic pain" encompasses the pain occurring in a wide range of disorders, for example, trauma, malignancies and chronic inflammatory diseases such as rheumatoid arthritis. Chronic pain may last more than about six months. In addition, the intensity of chronic pain may be disproportionate to the intensity of the noxious stimulus or underlying process. The term also refers to pain associated with a chronic disorder, or pain that persists beyond resolution of an underlying disorder or healing of an injury, and that is often more intense than the underlying process would predict. It may be subject to frequent recurrence.

As used herein, and unless otherwise specified, the term "inflammatory pain" is pain in response to tissue injury and the resulting inflammatory process. Inflammatory pain is adaptive in that it elicits physiologic responses that promote healing. However, inflammation may also affect neuronal function. Inflammatory mediators, including $PGE_2$ induced by the COX2 enzyme, bradykinins, and other substances, bind to receptors on pain-transmitting neurons and alter their function, increasing their excitability and thus increasing pain sensation. Much chronic pain has an inflammatory component. The term also refers to pain which is produced as a symptom or a result of inflammation or an immune system disorder.

As used herein, and unless otherwise specified, the term "visceral pain" refers to pain which is located in an internal organ.

As used herein, and unless otherwise specified, the term "mixed etiology pain" refers to pain that contains both inflammatory and neuropathic components.

As used herein, and unless otherwise specified, the term "dual mechanism pain" refers to pain that is amplified and maintained by both peripheral and central sensitization.

As used herein, and unless otherwise specified, the term "causalgia" refers to a syndrome of sustained burning, allodynia, and hyperpathia after a traumatic nerve lesion, often combined with vasomotor and sudomotor dysfunction and later trophic changes.

As used herein, and unless otherwise specified, the term "central pain" refers to pain initiated by a primary lesion or dysfunction in the central nervous system.

As used herein, and unless otherwise specified, the term "hyperesthesia" refers to increased sensitivity to stimulation, excluding the special senses.

As used herein, and unless otherwise specified, the term "hyperpathia" refers to a painful syndrome characterized by an abnormally painful reaction to a stimulus, especially a repetitive stimulus, as well as an increased threshold. It may occur with allodynia, hyperesthesia, hyperalgesia, or dysesthesia.

As used herein, and unless otherwise specified, the term "dysesthesia" refers to an unpleasant abnormal sensation, whether spontaneous or evoked. In certain embodiments, dysesthesia include hyperalgesia and allodynia.

As used herein, and unless otherwise specified, the term "hyperalgesia" refers to an increased response to a stimulus that is normally painful. It reflects increased pain on suprathreshold stimulation.

As used herein, and unless otherwise specified, the term "allodynia" refers to pain due to a stimulus that does not normally provoke pain.

As used herein, and unless otherwise specified, the term "Diabetic Peripheral Neuropathic Pain" (DPNP), also called diabetic neuropathy, DN or diabetic peripheral neuropathy), refers to chronic pain caused by neuropathy associated with diabetes mellitus. The classic presentation of DPNP is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, such as numbness.

As used herein, and unless otherwise specified, the term "Post-Herpetic Neuralgia", also called "Postherpetic Neuralgia (PHN)", refers to a painful condition affecting nerve fibers and skin. Without being limited by a particular theory, it is a complication of shingles, a second outbreak of the varicella zoster virus (VZV), which initially causes chickenpox.

As used herein, and unless otherwise specified, the term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

As used herein, and unless otherwise specified, the term "HIV/AIDS peripheral neuropathy" or "HIV/AIDS related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

As used herein, and unless otherwise specified, the term "Phantom Limb Pain" refers to pain appearing to come from where an amputated limb used to be. Phantom limb pain can also occur in limbs following paralysis (e.g., following spinal cord injury). "Phantom Limb Pain" is usually chronic in nature.

As used herein, and unless otherwise specified, the term "Trigeminal Neuralgia (TN)" refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

As used herein, and unless otherwise specified, the term "Complex Regional Pain Syndrome (CRPS)," formerly known as Reflex Sympathetic Dystrophy (RSD), refers to a chronic pain condition whose key symptom is continuous, intense pain out of proportion to the severity of the injury, which gets worse rather than better over time. The term encompasses type 1 CRPS, which includes conditions caused by tissue injury other than peripheral nerve, and type 2 CRPS, in which the syndrome is provoked by major nerve injury, and is sometimes called causalgia.

As used herein, and unless otherwise specified, the term "fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

As used herein, and unless otherwise specified, the term "convulsion" refers to a neurological disorder and is used interchangeably with "seizure," although there are many types of seizure, some of which have subtle or mild symptoms instead of convulsions. Seizures of all types may be caused by disorganized and sudden electrical activity in the brain. In some embodiments, convulsions are a rapid and uncontrollable shaking during which the muscles contract and relax repeatedly.

5.2 Compounds

Provided herein are compounds of formula (I):

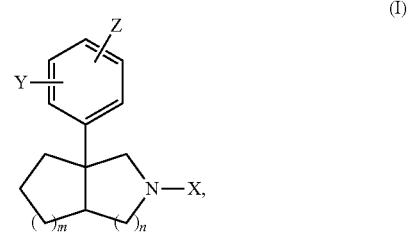

or a pharmaceutically acceptable salt, solvate, or stereoisomer thereof, wherein:

m is 0, 1, or 2;

n is 0, 1, or 2;

X is hydrogen, $(C_1-C_{10})$alkyl, $(C_3-C_{10})$cycloalkyl, $(C_3-C_{10})$cycloalkyl-$(C_1-C_{10})$alkyl, $(C_1-C_{10})$alkenyl, $(C_1-C_{10})$alkynyl, $(C_1-C_{10})$alkoxy, 6 to 10 membered aryl, (6 to 10 membered aryl)-($C_1$-$C_{10}$)alkyl, —$OR^1$, heteroalkyl, heteroalkenyl, or heteroalkynyl;

Y and Z are each independently halogen, —$CF_3$, —CN, —$NH_2$, —$NO_2$, dioxolano, ($C_1$-$C_{10}$)alkyl, ($C_3$-$C_{10}$)cycloalkyl, ($C_1$-$C_{10}$)alkenyl, ($C_1$-$C_{10}$)alkynyl, ($C_1$-$C_{10}$)alkoxy, ($C_3$-$C_{10}$)cycloalkoxy, or —$OR^2$; or Y and Z, taken together, may form 5, 6, or 7 membered cycloalkyl; and $R^1$ and $R^2$ are each independently hydrogen, ($C_1$-$C_{10}$)alkyl, ($C_1$-$C_{10}$)alkenyl, ($C_1$-$C_{10}$)alkynyl, ($C_3$-$C_{10}$)cycloalkyl, ($C_3$-$C_{10}$)cycloalkyl-($C_1$-$C_{10}$)alkyl, ($C_1$-$C_{10}$)alkoxy, 6 to 10 membered aryl, 6 to 10 membered heteroaryl, (6 to 10 membered aryl)-($C_1$-$C_{10}$)alkyl, —$SO_2$($C_1$-$C_{10}$)alkyl, or —$SO_2$-(6 to 10 membered aryl).

In one embodiment, m is 0. In another embodiment, m is 1. In another embodiment, m is 2.

In one embodiment, n is 0. In another embodiment, n is 1. In another embodiment, n is 2.

In one embodiment, X is hydrogen. In another embodiment, X is ($C_1$-$C_{10}$)alkyl. In another embodiment, X is ($C_3$-$C_{10}$)cycloalkyl. In another embodiment, X is ($C_3$-$C_{10}$)cycloalkyl-($C_1$-$C_{10}$)alkyl. In another embodiment, X is ($C_1$-$C_{10}$)alkenyl. In another embodiment, X is ($C_1$-$C_{10}$)alkynyl. In another embodiment, X is ($C_1$-$C_{10}$)alkoxy. In another embodiment, X is 6 to 10 membered aryl. In another embodiment, X is (6 to 10 membered aryl)-($C_1$-$C_{10}$)alkyl. In another embodiment, X is —$OR^1$. In another embodiment, X is heteroalkyl. In another embodiment, X is heteroalkenyl. In another embodiment, X is heteroalkynyl. In another embodiment, X is heterocycloalkyl.

In one embodiment where X is —$OR^1$, $R^1$ is hydrogen. In another embodiment, $R^1$ is ($C_1$-$C_{10}$)alkyl. In another embodiment, $R^1$ is ($C_1$-$C_{10}$)alkenyl. In another embodiment, $R^1$ is ($C_1$-$C_{10}$)alkynyl. In another embodiment, $R^1$ is ($C_3$-$C_{10}$)cycloalkyl. In another embodiment, $R^1$ is ($C_3$-$C_{10}$)cycloalkyl-($C_1$-$C_{10}$)alkyl. In another embodiment, $R^1$ is ($C_1$-$C_{10}$)alkoxy. In another embodiment, $R^1$ is 6 to 10 membered aryl. In another embodiment, $R^1$ is (6 to 10 membered aryl)-($C_1$-$C_{10}$)alkyl. In another embodiment, $R^1$ is-$SO_2$($C_1$-$C_{10}$)alkyl. In another embodiment, $R^1$ is —$SO_2$-(6 to 10 membered aryl).

In one embodiment, Y is halogen. In another embodiment, Y is —$CF_3$. In another embodiment, Y is —CN. In another embodiment, Y is —$NH_2$. In another embodiment, Y is —$NO_2$. In another embodiment, Y is dioxolano. In another embodiment, Y is ($C_1$-$C_{10}$)alkyl. In another embodiment, Y is ($C_3$-$C_{10}$)cycloalkyl. In another embodiment, Y is ($C_1$-$C_{10}$)alkenyl. In another embodiment, Y is ($C_1$-$C_{10}$)alkynyl. In another embodiment, Y is ($C_1$-$C_{10}$)alkoxy. In another embodiment, Y is ($C_3$-$C_{10}$)cycloalkoxy. In another embodiment, Y is —$OR^2$.

In one embodiment, Z is halogen. In another embodiment, Z is —$CF_3$. In another embodiment, Z is —CN. In another embodiment, Z is —$NH_2$. In another embodiment, Z is —$NO_2$. In another embodiment, Z is dioxolano. In another embodiment, Z is ($C_1$-$C_{10}$)alkyl. In another embodiment, Z is ($C_3$-$C_{10}$)cycloalkyl. In another embodiment, Z is ($C_1$-$C_{10}$)alkenyl. In another embodiment, Z is ($C_1$-$C_{10}$)alkynyl. In another embodiment, Z is ($C_1$-$C_{10}$)alkoxy. In another embodiment, Z is ($C_3$-$C_{10}$)cycloalkoxy. In another embodiment, Z is —$OR^2$.

In one embodiment, where Y and/or Z are —$OR^2$, $R^2$ is hydrogen. In another embodiment, $R^2$ is ($C_1$-$C_{10}$)alkyl. In another embodiment, $R^2$ is ($C_1$-$C_{10}$)alkenyl. In another embodiment, $R^2$ is ($C_1$-$C_{10}$)alkynyl. In another embodiment, $R^2$ is ($C_3$-$C_{10}$)cycloalkyl. In another embodiment, $R^2$ is ($C_3$-$C_{10}$)cycloalkyl-($C_1$-$C_{10}$)alkyl. In another embodiment, $R^2$ is ($C_1$-$C_{10}$)alkoxy. In another embodiment, $R^2$ is 6 to 10 membered aryl. In another embodiment, $R^2$ is (6 to 10 membered aryl)-($C_1$-$C_{10}$)alkyl. In another embodiment, $R^2$ is —$SO_2$($C_1$-$C_{10}$)alkyl. In another embodiment, $R^2$ is —$SO_2$-(6 to 10 membered aryl).

In one embodiment, Y and Z together form a 5 membered cycloalkyl. In one embodiment, Y and Z together form a 6 membered cycloalkyl. In one embodiment, Y and Z together form a 7 membered cycloalkyl.

Any of the combinations of m, n, X, Y, Z, $R_1$ and $R_2$ are encompassed by this disclosure and specifically provided herein.

In one embodiment, n is 1. In one embodiment where n is 1, m is 1 or 2.

In one embodiment, X is hydrogen. In another embodiment, X is ($C_1$-$C_{10}$)alkyl. In another embodiment, X is methyl. In another embodiment, X is ethyl.

In one embodiment, at least one of Y and Z are halogen. In another embodiment, Y and Z are both halogen. In another embodiment, Y and Z are both chloride.

Specific examples include, but are not limited to, the following compounds, or pharmaceutically acceptable salt, solvate, or stereoisomers thereof:

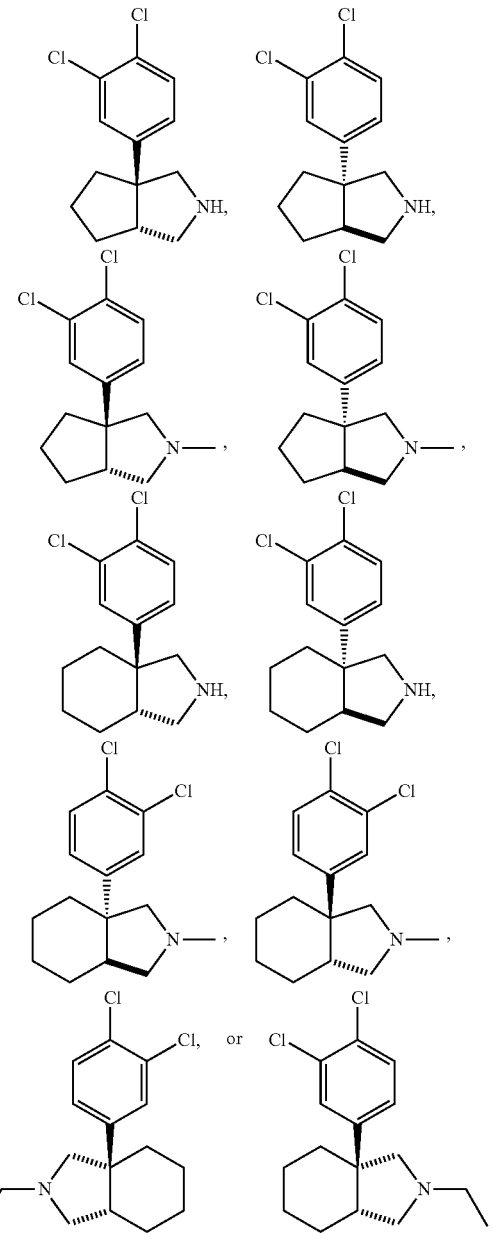

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.2.1 Synthetic Schemes

Five and six-membered ring aryl lactones can be synthesized via the lactone arylation procedures substantially similar to those disclosed in Malcolm et al., *Tetrahedron Lett.*, 46: 6871 (2005) to give dichloro analog 2a and 2b. Opening of lactone 2a/2b with lithium methylamide proceed in excellent yield to give alcohol 3a/3b, which is followed by borane reduction to give amino alcohol 4a/4b. An alternate procedure using methylamine in ethanol also provides good results in the ring-opening step. The procedures are summarized in Scheme 1, below:

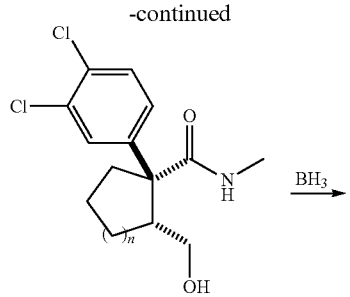

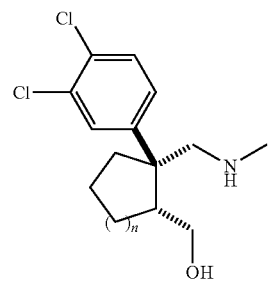

Amino alcohol 4a/4b are separated by chiral HPLC (e.g., AD-2:3:95:0.1 MeOH/EtOH/Hex/DEA) to give enantiomers 5a/b and 6a/b. Each enantiomer is then cyclized to provide the corresponding 5-5 and 6-5 bicyclic amines. The methylamine is demethylated using neat 1-chloroethyl chloroformate (CECF) to give 5-5 secondary amines and 6-5 secondary amines. Separation can be carried out using various methods known in the art. The procedures are summarized in Scheme 2, below:

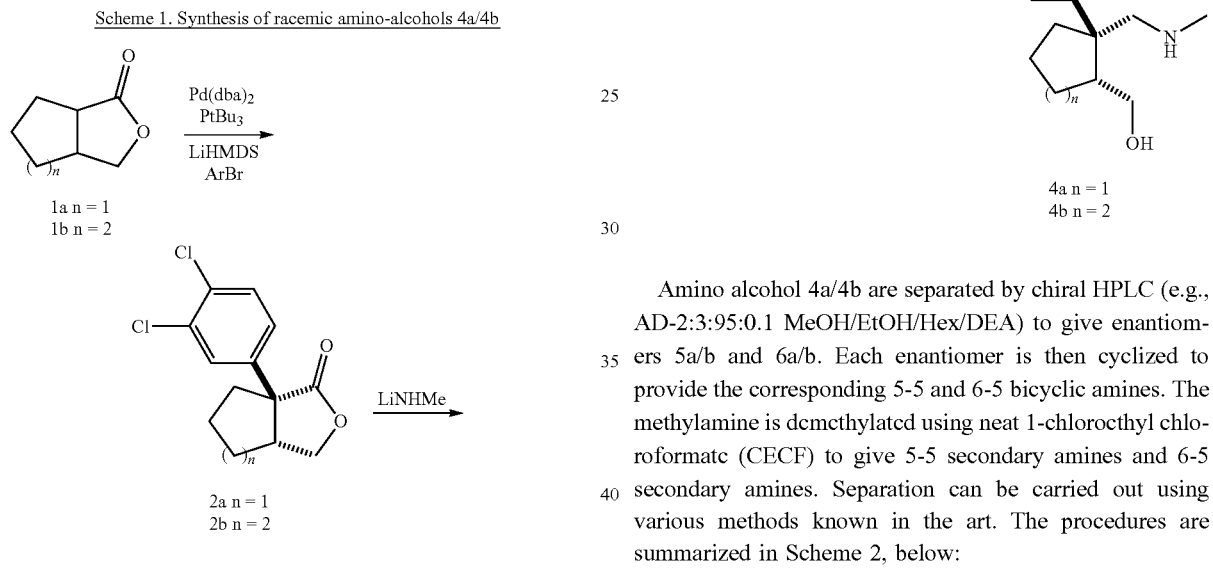

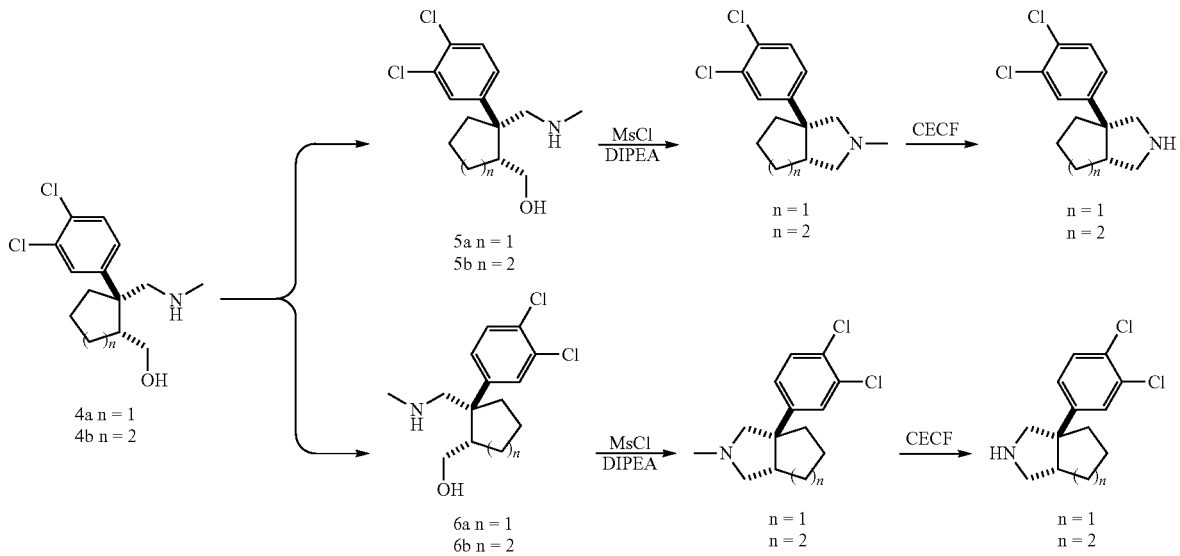

An alternative route to the racemic 6-5 bicyclic desmethyl amine (10, Scheme 3) was also developed that started from lactone 2b. Heating lactone 2b in the presence of potassium phthalimide provides amino acid 7, which can be converted directly to lactam 9 (via intermediate 8) after heating in KOH. Borane reduction of lactam 9 gave the desired racemic 6-5 desmethyl analog 10.

Scheme 3. Alternate route to racemic 6-5 desmethyl analogs

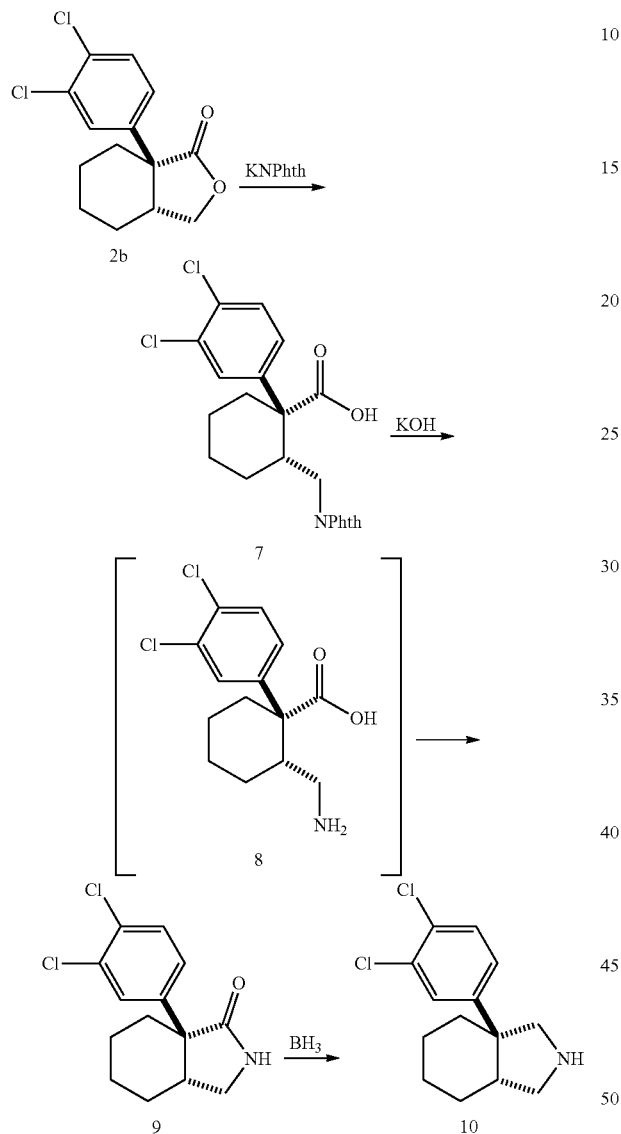

6-5 lactone 2b can be also used as the starting point for the synthesis of the N-ethyl substituted analogs (i.e., 13, Scheme 5). Opening of the lactone with ethylamine provides amide-alcohol 11, which is reduced with borane to give amino alcohol 12. Mesylation of 12 and intramolecular cyclization provides racemic N-ethyl product 13.

Scheme 5. Synthesis of N-ethyl analog 13

Racemic 6-5 bicyclic amine 10 can also be separated by chiral HPLC (e.g., Chiracel AD-95:5:0.1 hex/IPA/DEA) to give the corresponding enantiomers (Scheme 4).

Scheme 4. Chiral separation of desmethyl analog 10

Racemic 6-5 N-ethyl bicyclic amine 13 can be purified by chiral HPLC (e.g., Chiraltech OD, 95:5:0.05 hex/IPA/DEA) to give the corresponding enantiomers:

Scheme 6. Chiral separation of N-ethyl analog 13

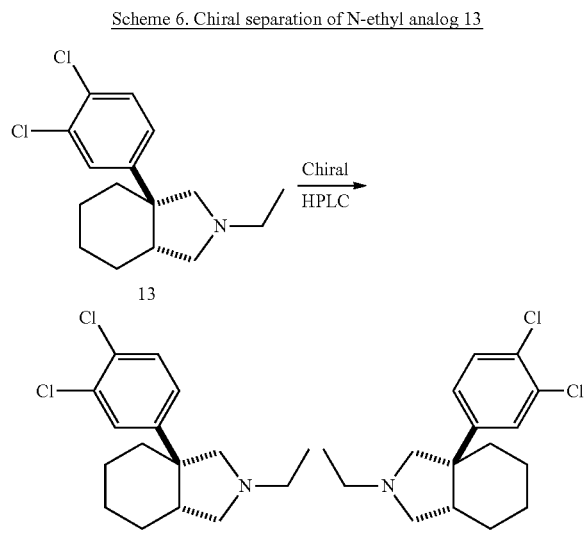

5.3 Methods of Treatment, Prevention, and/or Management

5.3.1 Binding to Monoamine Transporter

In various embodiments, provided herein is a method of binding a compound provided herein to a monoamine transporter. The method comprises contacting the monoamine transporter and a compound provided herein.

In other embodiments, provided herein is a method of inhibiting binding of a monoamine transporter ligand to a monoamine transporter (such as serotonin transporter, dopamine transporter and norepinephrine transporter). The method comprises contacting the monoamine transporter and a compound provided herein. In one embodiment the monoamine transporter ligand is an endogenous monoamine, such as serotonin, dopamine or norepinephrine. In another embodiment, the ligand is a drug molecule or another small molecule known to have binding affinity to a monoamine transporter. In another embodiment, the monoamine transporter ligand is a radioactively labeled compound, known to bind to the monoamine transporter.

In one embodiment, inhibition of ligand binding is assessed using an ex vivo binding assay, such as those described herein. In another embodiment, the compound provided herein inhibits mean binding by between about 1% and about 100%, between about 10% and about 100%, and between about 20% and about 90% when compared to vehicle. In one embodiment, inhibition of mean binding is dose dependent.

5.3.2 Inhibition of Monoamine Transporter Activity

In various embodiments, provided herein is a method of modulating (e.g., inhibiting, augmenting) the activity of at least one monoamine transporter, such as serotonin transporter, dopamine transporter and norepinephrine transporter. The method comprises contacting the monoamine transporter and a compound provided herein. In one embodiment, the monoamine transporter is contacted with a compound provided herein by administering to a subject a therapeutically effective amount of the compound provided herein, or a pharmaceutically acceptable salt or solvate thereof. The subject may be a human. In another embodiment, the monoamine transporter is dopamine transporter (DAT), serotonin transporter (SERT), or norepinephrine transporter (NET). In other embodiments, the compound provided herein inhibits the activity of at least two different monoamine transporters. Inhibition of monoamine transporter activity may be measured using assays known in the art. Exemplary assay methods include, but are not limited to, in vitro functional uptake assays. In one embodiment, the functional uptake assay utilizes an appropriate cell-line expressing a desired monoamine transporter. In other embodiments, the functional uptake assay utilizes synaptosomes isolated from brain tissue of an appropriate organism. In other embodiments, inhibition of monoamine transporter activity may be assessed using receptor binding experiments known in the art, e.g., utilizing appropriate membrane preparations. In one embodiment, the assay involves treatment of a test subject (e.g., a rat) with a compound provided herein as well as a reference compound, followed by isolation of brain tissue and ex vivo analysis of receptor occupancy, as described herein.

5.3.3 Inhibition of Monoamine Uptake

In some embodiments, provided herein is a method of inhibiting uptake of at least one monoamine (e.g., dopamine, serotonin, norepinephrine) by a cell. The method includes contacting the cell with a compound provided herein. In one embodiment, the cell is a brain cell, such as a neuron or a glial cell. In one embodiment, inhibition of monoamine uptake occurs in vivo. In an organism, neuronal uptake (also termed reuptake) of a monoamine such as dopamine or serotonin may occur, for example, from the synaptic cleft. Thus, in one embodiment, the neuronal cell is in contact with a synaptic cleft of a mammal. In another embodiment, inhibition of monoamine uptake occurs in vitro. In some embodiments, the cell may be a brain cell, such as a neuronal cell or a cell-type, which expresses a recombinant monoamine transporter.

In one embodiment, the compound inhibits uptake of at least two different monoamines. This can, for example, be shown by performing various in vitro functional uptake assays utilizing a cell-type, which simultaneously expresses multiple different monoamine transporters (such as isolated synaptosomes), or may be shown by using two different cell types, each expressing a different monoamine transporter, such as a recombinant dopamine transporter, together with an appropriate, labeled monoamine. In some embodiments, inhibition of monoamine uptake is demonstrated when the inhibitor (e.g., a compound provided herein) has an $IC_{50}$ of, for example, between about 0.1 nM and about 10 μM, between about 1 nM and about 1 μM, between about 1 nM and about 500 nM, and between about 1 nM and about 100 nM, in a functional monoamine uptake assay, such as those described herein below.

5.3.4 Treatment of Neurological Disorders

In some embodiments, provided herein is a method of treating, preventing, and/or managing a neurological disorder. Without being limited by a particular theory, the treatment, prevention, and/or management is done by inhibiting the activity of at least one monoamine transporter. The method comprises administering to a patient (e.g., human) a therapeutically or prophylactically effective amount of a composition or compound provided herein, or a pharmaceutically acceptable salt or solvate thereof. In one embodiment, the patient is a human. In another embodiment, the compound provided herein inhibits the activity of at least two different monoamine transporters. For example, the compound of the invention inhibits the activity of at least two of serotonin transporter, dopamine transporter and norepinephrine transporter. In some embodiments, inhibition of monoamine transporter activity may be assessed by functional monoamine uptake assays as described herein below.

Demonstration of compound activity can be performed in various art-recognized animal models. For example, anti-depressant activity of a compound may be assessed by utilizing an appropriate animal model of depression such as, but not limited to, the Rat Forced Swim Test, the Mouse Tail Suspension Test and Rat Locomotor Activity Analyses. The Rat Forced Swim Test is also suitable for the analysis of compounds having activities against more than one monoamine transporter (mixed monoamine transporter activity). For example, an increase in swimming activity is indicative of serotonin reuptake inhibition, while an increase in climbing activity is indicative of norepinephrine reuptake inhibition.

In some embodiments, the compounds provided herein are active in at least one animal model, which can be used to measure the activity of the compounds and estimate their efficacy in treating a neuroligal disorder. For example, when the animal model is for depression (e.g., mean immobility), the compounds are active when they inhibit mean immobility by between about 5% and about 90%, between about 10% and about 70%, between about 10% and about 50%, and between about 15% and about 50% in at least one animal model, when compared to vehicle. In some embodiments, the compounds provided herein produce a similar disparity in measured endpoint between treated animals and animals administered vehicle.

In other embodiments, provided herein is a method of effecting an anti-depressant-like effect. The method comprises administering to a subject (e.g., a mammal) a therapeutically effective amount of a compound or composition provided herein, or a pharmaceutically acceptable salt or solvate thereof. Anti-depressant-like effects may be measured using an animal model of disease, such as those known in the art and those described herein.

In some embodiments, the neurological disorder is: depression (e.g., major depressive disorder, bipolar disorder, unipolar disorder, dysthymia and seasonal affective disorder); cognitive deficits; fibromyalgia; pain (e.g., neuropathic pain); sleep related disorders (e.g., sleep apnea, insomnia, narcolepsy, cataplexy) including those sleep disorders which are produced by psychiatric conditions; chronic fatigue syndrome; attention deficit disorder (ADD); attention deficit hyperactivity disorder (ADHD); restless leg syndrome; schizophrenia; anxieties (e.g., general anxiety disorder, social anxiety disorder, panic disorder); obsessive compulsive disorder; posttraumatic stress disorder; seasonal affective disorder (SAD); premenstrual dysphoria; post-menopausal vasomotor symptoms (e.g., hot flashes, night sweats); neurodegenerative disease (e.g., Parkinson's disease, Alzheimer's disease and amyotrophic lateral sclerosis); manic conditions; dysthymic disorder; cyclothymic disorder; obesity; and substance abuse or dependency (e.g., cocaine addiction, nicotine addiction). In another embodiment, the compounds provided herein are useful to treat two or more conditions/disorders, which are comorbid, such as cognitive deficit and depression.

Neurological disorders include cerebral function disorders, including without limitation, senile dementia, Alzheimer's type dementia, cognition, memory loss, amnesia/amnestic syndrome, epilepsy, disturbances of consciousness, coma, lowering of attention, speech disorders, Lennox syndrome, autism, and hyperkinetic syndrome.

Neuropathic pain includes without limitation post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

Other exemplary diseases and conditions that may be treated, prevented, and/or managed using the methods, compounds, and/or compositions provided herein include, but are not limited to: obesity; migraine or migraine headache; urinary incontinence, including without limitation involuntary voiding of urine, dribbling or leakage of urine, stress urinary incontinence (SUI), urge incontinence, urinary exertional incontinence, reflex incontinence, passive incontinence, and overflow incontinence; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dyspareunia, functional vaginismus, and atypical psychosexual dysfunction.

In one embodiment, the neurological disorder is depression. In another embodiment, the neurological disorder is anxiety disorder. In another embodiment, the neurological disorder is pain. In another embodiment, the neurological disorder is neuropathic pain. In another embodiment, the neuropathic pain is diabetic neuropathy.

In one embodiment, the neurological disorder is a neurodegenerative disease. In one embodiment, the neurodegenerative disease is Parkinson's disease. In another embodiment, the neurodegenerative disorder is Alzheimer's disease.

In one embodiment, the neurological disorder is incontinence, for example, urinary incontinence. In another embodiment, the neurological disorder is sexual dysfunction.

In one embodiment, the neurological disorder is obesity, and the therapeutically effective amount of compound to supply to a patient is sufficient so that said patient feels satiated.

In one embodiment, the compounds described herein treat, prevent, and/or manage a central nervous disorder, without causing addiction to said compounds.

Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Exemplary routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. An exemplary transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

The amount to be administered to a patient to treat, prevent, and/or manage the disorders described herein will depend upon a variety of factors including the activity of the particular compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound provided herein will be that amount of the compound which is the lowest dose effective to produce a therapeutic or prophylactic effect. Such an effective dose will generally depend upon the factors described above. Generally, oral, intravenous, intracerebroventricular and subcutaneous doses of the compounds provided herein for a patient will range from about 0.005 mg per kilogram to about 5 mg per kilogram of body weight per day. In one embodiment, the oral dose of a compound provided herein will range from about 10 mg to about 300 mg per day. In another embodiment, the oral dose of a compound provided herein will range from about 20 mg to about 250 mg per day. In another embodiment, the oral dose of a compound provided herein will range from about 100 mg to about 300 mg per day. In another embodiment, the oral dose of a compound provided herein will range from about 10 mg to about 100 mg per day. In another embodiment, the oral dose of a compound provided herein will range from about 25 mg to about 50 mg per day. In another embodiment, the oral dose of a compound provided herein will range from about 50 mg to about 200 mg per day. Each of the above-recited dosage ranges may be formulated as a single or multiple unit dosage formulations.

In some embodiments, the compounds disclosed herein may be used in combination with one or more second active agents to treat, prevent, and/or manage disorders described herein. Examples of such second active agents are also provided herein elsewhere.

5.4 Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, solvate, stereoisomer, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are also disclosed herein.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., *Remington's Pharmaceutical Sciences,* 18th ed., Mack Publishing, Easton Pa. (1990).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose or other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise a compound provided herein in an amount of from about 0.10 to about 500 mg. In other embodiments, dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

5.4.1 Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form. Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, anhydrous lactose, microcrystalline cellulose, polyvinylpyrrolidone, stearic acid, colloidal anhydrous silica, and gelatin.

5.4.2 Controlled Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and U.S. Pat. Nos. 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.4.3 Parenteral Dosage Forms

Parenteral dosage forms can be administered to patients by various routes including, but not limited to, subcutaneous, intravenous (including bolus injection), intramuscular, and intraarterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

5.4.4 Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., *Remington's Pharmaceutical Sciences,* 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, prodrugs, clathrates, or stereoisomers of the active ingredients can be used to further adjust the properties of the resulting composition.

5.5 Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise one or more second active ingredients as described herein, or a pharmacologically active mutant or derivative thereof, or a combination thereof.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

6. EXAMPLES

Certain embodiments are illustrated by the following non-limiting examples.

6.1 Synthesis of Compounds

6.1.1 6a-(3,4-Dichlorophenyl)hexahydro-1H-cyclopenta[c]furan-1-one and 7a-(3,4-Dichlorophenyl)hexahydroisobenzofuran-1(3H)-one

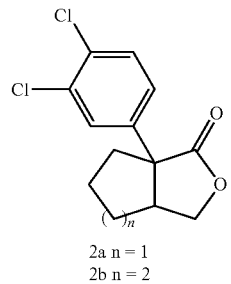

2a n = 1
2b n = 2

2a: To a solution of lactone (hexahydro-1H-cyclopenta[c]furan-1-one, 630 mg, 5 mmol), palladium dba (145 mg, 5 mol %) and toluene (6 mL), which was stirring under nitrogen in a sealed vial, were added tri-t-butylphosphine (250 μL, 5 mol %), lithium HMDS (6 mL, 1.2eq), and dichlorophenylbromide (1.69 g, 1.5eq). The solution was heated in the microwave for fifteen minutes (max temp=140° C.). After cooling, the mixture was diluted with hexane, washed with 3M HCl, and evaporated. The crude brown oil was purified on silica gel to give 2a (578 mg, 44%) as a pale-brown oil. TLC $R_f$ (25% EA/hex)=0.34. GC-MS $R_t$=12.48 min, m/z=270 (M+). $^1$H NMR (CDCl$_3$, δ): 7.49 (d, J=2.3 Hz, 1H), 7.41 (d, J=8.4 Hz, 1H), 7.24 (dd, J=2.3, 8.4 Hz, 1H), 4.50 (dd, J=7.3, 9.6 Hz, 1H), 4.14 (dd, J=2.2, 9.6 Hz, 1H), 3.1 (m, 1H), 2.60 (ddd, J=3.0, 6.4, 12.5 Hz, 1H), 2.2-1.6 (m, 5H). $^{13}$C NMR (CDCl$_3$, δ, mult): 179.7 (0), 140.6 (0), 132.8 (0), 131.5 (0), 130.6 (1), 128.3 (1), 125.8 (1), 72.7 (2), 59.4 (0), 46.2 (1), 40.3 (2), 34.4 (2), 25.8 (2).

2b: To a flame-dried 250 mL round bottom flask was added Pd(dba)$_2$ (368 mg, 1 mol %) and toluene. The vessel was purged with nitrogen and sealed before tri-t-butylphosphine (704 μL, 1M in toluene, 1.1 mol %) was added via syringe followed by phenyl bromide (5.4 mL, 51.27 mmol) as a solution in toluene (15 mL). LiHMDS (64 mL, 1.3 eq) was added and the light brown solution was stirred at ambient temperature for 15 minutes. Hexahydroisobenzofuran-1(3H)-one (10 g, 1.3eq) was added dropwise as a solution in toluene (20 mL). At this point an exotherm was noted followed by the formation of a light colored precipitate. The mixture was allowed to stir at ambient temperature overnight (16 hours) and then partitioned between hexane and, in succession, 10% aqueous HCl, 10% aqueous K$_2$CO$_3$, and brine. The volatile components were removed in vacuo to give the crude arylated lactone as a brown-green oil (12.6 g). Separation of the unreacted lactone using a 120 g Redisep cartridge gave the title compound as a yellow oil (7.40 g, 67%). HPLC $R_t$=9.8 min. $^1$H NMR (CDCl$_3$, δ): 7.4-7.2 (m, 5H), 4.05 (dd, 1H), 3.90 (dd, 1H), 2.8 (m, 1H), 2.3 (m, 1H), 2.0 (m, 1H), 1.8-1.3 (m, 6H). $^{13}$C NMR (CDCl$_3$, δ, mult): 178.6 (0), 140.5 (0), 128.8 (1), 127.3 (1), 126.3 (1), 70.3 (2), 52.5 (0), 41.0 (1), 34.2 (2), 27.5 (2), 23.4 (2), 23.2 (2).

6.1.2 1-(3,4-Dichlorophenyl)-2-(hydroxymethyl)-N-methylcyclopentane carboxamide and 1-(3,4-Dichlorophenyl)-2-(hydroxymethyl)-N-methylcyclohexanecarboxamide

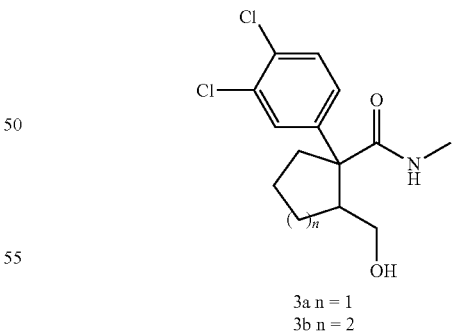

3a n = 1
3b n = 2

3a: To a solution of methylamine (1.5 mL, 2M in THF, 2eq) at −78° C. was added n-BuLi (1.2 mL, 2.5M in hexanes, 2eq) dropwise. After 5 minutes, a solution of the 2a (413 mg, 1.529 mmol) in THF (3 mL) was added in one portion. The mixture was stirred at low temperature for 5 minutes and at ambient temperature for 2 hours. The solution was quenched with NH$_4$Cl, extracted with MTBE, and evaporated. The residue was purified on silica to give methylamide 3a as a pale-yellow oil (351.0 mg, 76%). TLC $R_f$ (50% EA/hex) =0.13. GC-MS $R_t$=12.4 min, m/z=283 (M-H$_2$O). $^1$H NMR (CDCl$_3$, δ): 7.51 (d, J=2.3 Hz, 1H), 7.40 (d, J=8.5 Hz, 1H), 7.25 (dd, J=2.3, 8.5 Hz, 1H), 3.8 (bs, 1H), 3.7 (m, 2H), 3.5 (s, 1H), 2.73 (d, J=4.8 Hz, 3H), 2.7-2.4 (m, 2H), 2.1-1.5 (m, 5H). $^{13}$C NMR (CDCl$_3$, δ, mult): 175.7 (0), 144.4 (0), 132.5 (0), 131.0 (0), 130.4 (1), 129.1 (1), 126.8 (1), 63.9 (2), 61.3 (0), 50.0 (1), 37.9 (2), 27.8 (2), 26.7 (3), 22.1 (2).

Using similar procedures, 3b was also made from 2b.

6.1.3 (2-(3,4-Dichlorophenyl)-2-((methylamino)methyl) cyclopentyl) methanol and (2-(3,4-Dichlorophenyl)-2-((methylamino)methyl) cyclohexyl)methanol

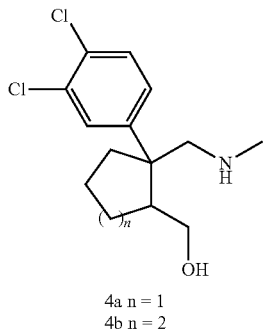

4a n = 1
4b n = 2

4a: To a solution of amide 3a (110 mg, 0.4412 mmol) in THF (1.3 mL) was added borane-THF (1.3 mL). After two minutes, the solution was heated in the microwave for 30 minutes (max temp=100° C.). After cooling, the reaction was quenched cautiously with a few drops of methanol followed by 3N HCl (4 mL) and stirred for 30 minutes. The solution was washed with 50% MTBE/hexanes, chilled, basified with KOH, and extracted with MTBE. After evaporation, the compound was filtered through an aminopropyl cartridge to give amine 4a (315.9 mg, 95% yield) as a pale-yellow oil. LCMS (14 min) $R_t$=5.98 min, m/z=288 (M+1). $^1$H NMR (CDCl$_3$, δ): 7.6 (m, 1H), 7.4 (m, 2H), 6.8 (bs, 1H), 3.7 (m, 2H), 2.8 (m, 3H), 2.32 (s, 3H), 2.1-1.2 (m, 6H). $^{13}$C NMR (CDCl$_3$, δ, mult): 147.3 (0), 132.5 (0), 130.2 (1), 130.1 (1), 129.3 (0), 126.9 (1), 63.7 (2), 58.3 (2), 52.9 (0), 47.1 (1), 41.6 (2), 36.0 (3), 28.6 (2), 22.1 (2).

Using similar procedures, 4b was made from 3b.

6.1.4 ((1R,2S)-2-(3,4-Dichlorophenyl)-2-((methylamino) methyl) cyclopentyl)methanol (5a), ((1R,2S)-2-(3,4-dichlorophenyl)-2-((methylamino)methyl)cyclohexyl)methanol (6a), ((1S,2R)-2-(3,4-Dichlorophenyl)-2-((methylamino) methyl)cyclopentyl)methanol (5b), and ((1S,2R)-2-(3,4-dichlorophenyl)-2-((methylamino) methyl)cyclohexyl)methanol

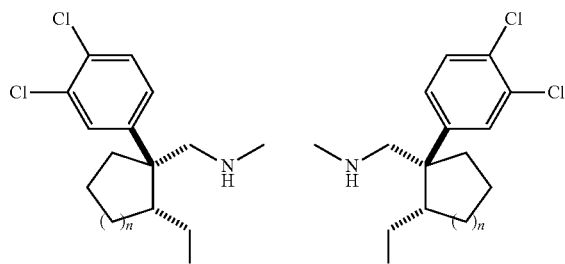

5a n = 1
5b n = 2

6a n = 1
6b n = 2

Compounds 4a was separated by chiral HPLC (AD-2:3: 95:0.1 MeOH/EtOH/Hex/DEA) to provide the products 5a and 6a. Using similar procedures, compound 4b was separated into compounds 5b and 6b.

6.1.5 (3aS,6aR)-3a-(3,4-Dichlorophenyl)-2-methyloctahydrocyclopenta[c]pyrrole and (3aR,6aS)-3a-(3,4-Dichlorophenyl)-2-methyl octahydrocyclopenta[c]pyrrole

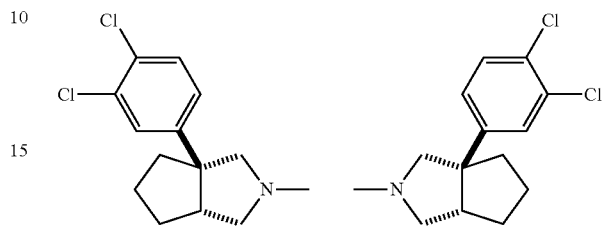

Aminol 5a (47.3 mg, 0.164 mmol) was dissolved in 1 mL DCM and allowed to react with mesyl chloride (19 μL, 1.5eq) in the presence of diisopropylethylamine (86 μL, 3eq) for two hours. The mixture was quenched with aqueous potassium carbonate and extracted with MTBE. The crude residue after evaporation was passed through an aminopropyl column to provide (3aS,6aR)-3a-(3,4-dichlorophenyl)-2-methyloctahydro cyclopenta[c]pyrrole (43.5 mg, 99%) as a clear oil. LCMS $R_t$=8.56 min m/z=270 (M+1). $^1$H NMR (CDCl$_3$, δ): 7.41 (d, J=2.3 Hz, 1H), 7.34 (d, J=8.5 Hz, 1H), 7.17 (dd, J=2.3, 8.4 Hz, 1H), 2.87 (t, J=8.4 Hz, 1H), 2.7 (m, 1H), 2.6 (m, 2H), 2.3 (m, 1H), 2.32 (s, 3H), 2.0-1.5 (m, 6H). $^{13}$C NMR (CDCl$_3$, δ, mult): 150.4 (0), 131.9 (0), 129.9 (1), 128.2 (1), 125.7 (1), 70.4 (2), 64.6 (2), 58.3 (0), 50.2 (1), 42.0 (3), 41.0 (2), 33.6 (2), 25.8 (2).

(3 aR,6aS)-3a-(3,4-Dichlorophenyl)-2-methyloctahydrocyclopenta[c]pyrrole was also made using similar procedures, and using aminol 6a as a starting compound.

6.1.6 (3aS,6aR)-3a-(3,4-Dichlorophenyl)octahydrocyclopenta[c]pyrrole and (3aR,6aS)-3a-(3,4-Dichlorophenyl)octahydrocyclopenta[c]pyrrole

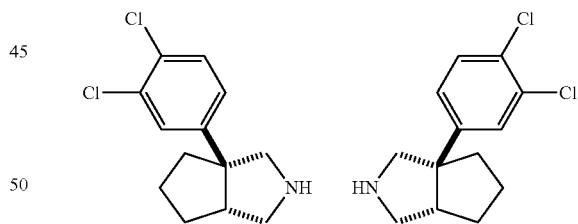

(3aS,6aR)-3a-(3,4-Dichlorophenyl)-2-methyloctahydrocyclopenta[c]pyrrole (20 mg) was dissolved in 1-chloroethyl chloroformate (250 μL) and heated to 80° C. for 15 hours. The reaction was cooled and evaporated. The residue was dissolved in methanol and heated at 80° C. for an additional 3 hours. After evaporation, the residue was diluted in DCM, washed with K$_2$CO$_3$, and filtered (aminopropyl cartridge). (3aS,6aR)-3a-(3,4-Dichlorophenyl)octahydrocyclopenta[c] pyrrole was then separated from unreacted starting material by chromatography (Chiraccl AD; 95:5:0.1 IPA/Hex/DEA). LCMS $R_t$=7.14 min m/z=256 (M+1). $^1$H NMR (CDCl$_3$, δ): 7.3 (m, 2H), 7.12 (dd, J=2.3, 8.4 Hz, 1H), 3.3 (m, 1H), 3.00 (s, 2H), 2.7 (m, 2H), 2.0-1.9 (m, 3H), 1.8-1.5 (m, 2H), 1.5 (m, 1H). $^{13}$C NMR (CDCl$_3$, δ, mult): 150.2 (0), 132.1 (0), 130.0 (1), 129.4 (0), 128.1 (1), 125.7 (1), 62.2 (2), 60.0 (0), 56.1 (2), 50.7 (1), 40.5 (2), 33.7 (2), 25.8 (2).

(3aR,6aS)-3a-(3,4-Dichlorophenyl)octahydrocyclopenta[c]pyrrole was made using similar procedures, using (3aR,6aS)-3a-(3,4-dichlorophenyl)-2-methyloctahydrocyclopenta[c]pyrrole as a starting compound.

6.1.7 (3aS,7aR)-3a-(3,4-Dichlorophenyl)-2-methyloctahydro-1H-isoindole and (3aR,7aS)-3a-(3,4-Dichlorophenyl)-2-methyloctahydro-1H-isoindole

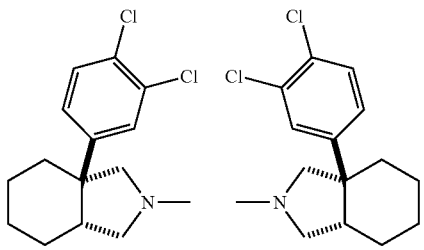

Amino alcohol 5b (40 mg, 0.1323 mmol) was dissolved in DCM (1 mL) and stirred at ambient temperature. To this solution was added DIPEA (70 µL, 3eq) and MSCl (15 µL, 1.5eq). After 2 hours, the reaction was quenched with potassium carbonate and extracted with MTBE. The organic phase was separated and evaporated. The residue was dissolved in DCM, filtered (aminopropyl) and evaporated to give (3aS,7aR)-3a-(3,4-Dichlorophenyl)-2-methyloctahydro-1H-isoindole (28.3 mg, 75%) as a clear oil. LCMS $R_t$=8.20 min, m/z=284 (M+1). $^1$H NMR (CDCl$_3$, δ): 7.43 (d, J=2.3 Hz, 1H), 7.37 (d, J=8.5 Hz, 1H), 7.19 (dd, J=2.3, 8.5 Hz, 1H), 2.9 (m, 2H), 2.78 (t, J=9.2 Hz, 1H), 2.7-2.6 (m, 2H), 2.42 (s, 3H), 2.0-1.8 (m, 2H), 1.8-1.6 (m, 2H), 1.6-1.4 (m, 3H), 1.2-1.0 (m, 1H). $^{13}$C NMR (CDCl$_3$, δ, mult): 146.9 (0), 132.2 (0), 130.1 (1), 129.8 (0), 128.8 (1), 126.1 (1), 69.8 (2), 58.8 (2), 47.7 (0), 43.3 (3), 40.5 (1), 34.3 (2), 24.6 (2), 21.7 (2), 20.9 (2).

(3aR,7aS)-3a-(3,4-Dichlorophenyl)-2-methyloctahydro-1H-isoindole was prepared using similar procedures, and using amino alcohol 6b as a starting compound.

6.1.8 7a-(3,4-Dichlorophenyl)octahydro-1H-isoindol-1-one

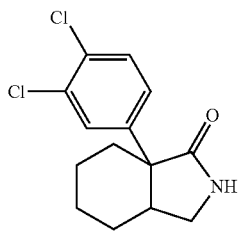 [SMILES: O=C1NCC2CCCCC12c1ccc(Cl)c(Cl)c1]

A mixture of dichlorophenyl lactone 2b (580 mg, 2.049 mmol), potassium phthalimide (758 mg, 2eq), and DMF (4 mL) was stirred in a 150° C. bath for 24 hours. Evaporation gave the crude acid. The crude material from above was diluted with 5M KOH (10 mL) and heated in a 110° C. bath for 24 hours. Extraction with ethyl acetate followed by evaporation gave the crude lactam. Separation on silica gel gave pure 7a-(3,4-dichlorophenyl)octahydro-1H-isoindol-1-one (67.5 mg, 12%) as a clear oil. TLC $R_f$ (50% EA/hex) =0.25. GC-MS $R_t$=13.77 min, m/z=283 (M−1). LCMS R, =9.09 min. HPLC $R_t$=10.15 train. $^1$H NMR (CDCl$_3$/DMSO-D6, δ): 7.37 (d, J=2.3 Hz, 1H), 7.25 (d, J=8.5 Hz, 1H), 7.14 (dd, J=2.3, 8.5 Hz, 1H), 4.02 (s, 1H), 3.07 (dd, J=5.8, 9.9 Hz, 1H), 2.83 (dd, J=3.6, 9.9 Hz, 1H), 2.6 (m, 1H), 1.9 (m, 1H), 1.7 (m, 1H), 1.6-1.2 (m, 6H). $^{13}$C NMR (CDCl$_3$/DMSO-D6, δ, mult): 179.3 (0), 142.5 (0), 132.2 (0), 130.6 (0), 130.1 (1), 128.8 (1), 126.2 (1), 51.6 (0), 44.2 (2), 40.3 (1), 32.6 (2), 26.9 (2), 22.7 (2), 22.6 (2).

6.1.9 3a-(3,4-Dichlorophenyl)octahydro-1H-isoindole

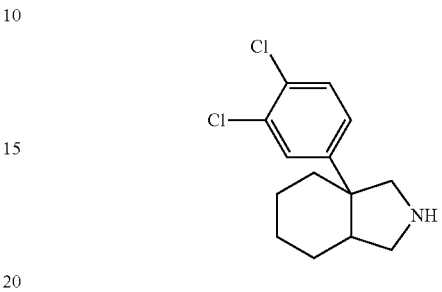

7a-(3,4-Dichlorophenyl)octahydro-1H-isoindol-1-one (65 mg, 0.2287 mmol) was diluted in THF (2 mL) and borane (0.7 mL, 1 M in THF, 3eq) and heated in the microwave for 15 minutes (max temp=100° C.). After cooling, the mixture was stirred with 6N HCl for thirty minutes and washed with MTBE. The aqueous layer was basicified with KOH and extracted with MTBE. The organic phase was evaporated and filtered (aminopropyl cartridge) to give 3a-(3,4-dichlorophenyl)octahydro-1H-isoindole (15.5 mg, 24%) as a clear oil. A further portion was later found in the organic wash and separated by silica gel filtration to give 19 mg (26%) additional product. LCMS $R_t$=7.60 min, m/z=270 (M+1). $^1$H NMR (CDCl$_3$, δ): 7.43 (d, J=2.3 Hz, 1H), 7.37 (d, J=8.4 Hz, 1H), 7.19 (dd, J=2.3, 8.5 Hz, 1H), 3.1 (m, 2H), 2.9 (m, 1H), 2.6 (m, 2H), 2.0-1.2 (m, 8H). $^{13}$C NMR (CDCl$_3$, δ, mult): 146.7 (0), 132.3 (0), 130.1 (1), 129.7 (0), 128.9 (1), 126.2 (1), 59.9 (2), 49.6 (2), 47.9 (0), 41.0 (1), 32.8 (2), 24.2 (2), 22.0 (2), 21.4 (2).

Racemic 3a-(3,4-dichlorophenyl)octahydro-1H-isoindole was separated by chiral HPLC (Chiracel AD-95:5:0.1 Hex/IPA/DEA) to provide the isomers (3aS,7aR)-3a-(3,4-dichlorophenyl)octahydro-1H-isoindole and (3aR,7aS)-3a-(3,4-dichlorophenyl)octahydro-1H-isoindole:

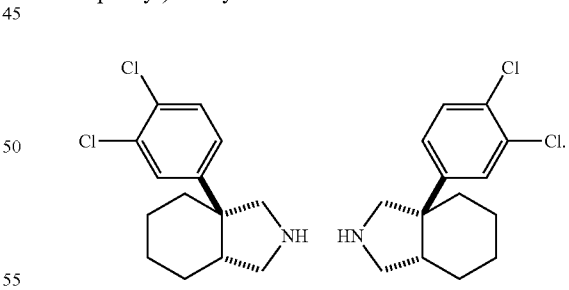

6.2 Monoamine Reuptake Assays

The compounds disclosed herein were tested for their inhibition of functional uptake of serotonin (5-HT), norepinephrine (NE), and dopamine (DA), using recombinant human transporters, as described herein below. Compounds were initially tested at 10 µM in duplicate. Compounds showing equal to or higher than 50% inhibition of uptake were further tested at 10 different concentrations in duplicate in order to obtain full inhibition curves. IC$_{50}$ values (concentration inhibiting control activity by 50%) were then determined by nonlinear regression analysis of the inhibition curves.

6.2.1 Serotonin Functional Uptake Assay for Human Reuptake Transporter

Inhibition of human serotonin reuptake transporter was assayed using the recombinant human serotonin transporter expressed in HEK-293 cells using a method substantially similar to that described in Gu H et al., *J. Biol. Chem.* 1994, 269 (10): 7124-7130, incorporated herein by reference. HEK-293 cells expressing human serotonin transporter were plated before the assay. Test compound and/or vehicle was preincubated with cells in modified HEPES buffer pH 7.1 or pH 7.4 for 20 minutes at 18 to 25° C., and 65 nM [$^3$H] serotonin was then added for an additional timed incubation period (ten to thirty minutes). Cells with internalized [$^3$H] serotonin were washed, and the amount of tritium taken into cells is counted using a liquid scintillation counter to determine [$^3$H]serotonin uptake. Non-specific binding of tritium was measured in a control reaction containing 10 µM fluoxetine, and was subtracted from the counts for assays to correct for non-specific binding of tritium. Reduction of [$^3$H]serotonin uptake by 50 percent or more relative to an uninhibited control reaction indicates significant inhibitory activity. Compounds were screened at 10, 1, 0.1, 0.01 and 0.001 µM.

6.2.2 Norepinephrine Functional Uptake Assay for Human Reuptake Transporter Inhibition of human norepinephrine reuptake transporter was assayed using the recombinant human norepinephrine transporter expressed in either HEK293 or MDCK cells using a method substantially similar to that described in Galli A et al., *J. Exp. Biol.* 198: 2197-2212 (1995), incorporated herein by reference. The cells were plated before the assay. Test compound and/or vehicle was preincubated with cells in modified HEPES buffer pH 7.1 or pH 7.4 for 20 minutes at 18 to 25° C. Following the preincubation, 25 nM [$^3$H]norepinephrine was added for an additional timed incubation period (10 to 20 minutes). After the cells were washed to remove [$^3$H]norepinephrine not internalized, the cells were lysed, and the amount of tritium in the cell lysate was measured using a liquid scintillation counter to determine [$^3$H]norepinephrine uptake. Non-specific binding of tritium was measured in a control reaction containing 10 µM imipramine (or 10 µM nisoxctine), and was subtracted from the counts for assays to correct for non-specific binding of tritium. Reduction of [$^3$H]norepinephrine uptake by 50 percent or more relative to an uninhibited control reaction indicates significant inhibitory activity. Compounds were screened at 10, 1, 0.1, 0.01 and 0.001 µM.

6.2.3 Dopamine Functional Uptake Assay for Human Reuptake Transporter

Inhibition of human dopamine reuptake transporter was assayed using the recombinant human dopamine transporter expressed in either CHO-K1 or HEK293 cells using a method substantially similar to that described in Pristupa, Z. B. et al., *Mol. Pharmacol.* 45: 125-135 (1994), incorporated herein by reference. Either CHO-K1 or HEK293 cells expressing human recombinant dopamine transporter were plated before the assay. Test compound and/or vehicle was preincubated with cells in modified HEPES buffer pH 7.1 or pH 7.4 for 20 minutes at 18 to 25° C., and 50 nM [$^3$H]dopamine was then added for an additional timed incubation period (10 to 30 minutes). After washing the cells to remove [$^3$H]dopamine not internalized, the cells were lysed, and the amount of tritium in the lysate was measured using a liquid scintillation counter to determine [$^3$H]dopamine uptake. Non-specific binding of tritium was measured in a control reaction containing 10 µM nomifensine, and was subtracted from the counts for assays to correct for non-specific binding of tritium. Reduction of [$^3$H]dopamine uptake by 50 percent or more relative to an uninhibited control reaction indicates significant inhibitory activity. Compounds were screened at 10, 1, 0.1, 0.01 and 0.001 µM.

6.2.4 Results

6.2.4.1 Serotonin Uptake Inhibition

Certain compounds provided herein were tested for serotonin reuptake inhibition using the procedures described in Section 6.2.1 above. Tested compounds included: (3aS,6aR)-3a-(3,4-dichlorophenyl)octahydrocyclopenta[c]pyrrole; (3aR,6aS)-3a-(3,4-dichlorophenyl)octahydrocyclopenta[c]pyrrolo; (3aS,6aR)-3a-(3,4-dichlorophenyl)-2-methyloctahydrocyclopenta[c]pyrrole; (3aR,6aS)-3a-(3,4-dichlorophenyl)-2-methyloctahydrocyclopenta[c]pyrrole; (3aS,7aR)-3a-(3,4-dichlorophenyl)octahydro-1H-isoindole; (3aR,7aS)-3a-(3,4-dichlorophenyl)octahydro-1H-isoindole; (3aR,7aS)-3a-(3,4-dichlorophenyl)-2-methyloctahydro-1H-isoindole; (3aS,7aR)-3a-(3,4-dichlorophenyl)-2-methyloctahydro-1H-isoindole; (3aR,7aS)-3a-(3,4-dichlorophenyl)-2-ethyloctahydro-1H-isoindole; and (3aS,7aR)-3a-(3,4-dichlorophenyl)-2-ethyloctahydro-1H-isoindole. The IC$_{50}$ values obtained from these compounds ranged from 3 to 551 nM.

6.2.4.2 Norepinephrine Uptake Inhibition

Certain compounds provided herein were tested for norepinephrine reuptake inhibition using the procedures described in Section 6.2.2 above. Tested compounds included: (3aS,6aR)-3a-(3,4-dichlorophenyl)octahydrocyclopenta[c]pyrrole; (3aR,6aS)-3a-(3,4-dichlorophenyl)octahydrocyclopenta[c]pyrrole; (3aS,6aR)-3a-(3,4-dichlorophenyl)-2-methyloctahydrocyclopenta[c]pyrrole; (3aR,6aS)-3a-(3,4-dichlorophenyl)-2-methyloctahydrocyclopenta[c]pyrrole; (3aS,7aR)-3a-(3,4-dichlorophenyl)octahydro-1H-isoindole; (3aR,7aS)-3a-(3,4-dichlorophenyl)octahydro-1H-isoindole; (3aR,7aS)-3a-(3,4-dichlorophenyl)-2-methyloctahydro-1H-isoindole; (3aS,7aR)-3a-(3,4-dichlorophenyl)-2-methyloctahydro-1H-isoindole; (3aR,7aS)-3a-(3,4-dichlorophenyl)-2-ethyloctahydro-1H-isoindole; and (3aS,7aR)-3a-(3,4-dichlorophenyl)-2-ethyloctahydro-1H-isoindole. The IC$_{50}$ values obtained from these compounds ranged from 13 to 212 nM.

6.2.4.3 Dopamine Uptake Inhibition

Certain compounds provided herein were tested for serotonin reuptake inhibition using the procedures described in Section 6.2.3 above. Tested compounds included: (3aS,6aR)-3a-(3,4-dichlorophenyl)octahydrocyclopenta[c]pyrrole; (3aR,6aS)-3a-(3,4-dichlorophenyl)octahydrocyclopenta[c]pyrrole; (3aS,6aR)-3a-(3,4-dichlorophenyl)-2-methyloctahydrocyclopenta[c]pyrrole; (3aR,6aS)-3a-(3,4-dichlorophenyl)-2-methyloctahydrocyclopenta[c]pyrrole; (3aS,7aR)-3a-(3,4-dichlorophenyl)octahydro-1H-isoindole; (3aR,7aS)-3a-(3,4-dichlorophenyl)octahydro-1H-isoindole; (3aR,7aS)-3a-(3,4-dichlorophenyl)-2-methyloctahydro-1H-isoindole; (3aS,7aR)-3a-(3,4-dichlorophenyl)-2-methyloctahydro-1H-isoindole; (3aR,7aS)-3a-(3,4-dichlorophenyl)-2-ethyloctahydro-1H-isoindole; and (3aS,7aR)-3a-(3,4-dichlorophenyl)-2-ethyloctahydro-1H-isoindole. The IC$_{50}$ values obtained from these compounds ranged from 7 to 254 nM.

6.3 Metabolic Stability

The liver is the main organ of drug metabolism in the body. Certain compounds provided herein were tested for microsomal stability using the following procedures:

Subcellular fractions such as liver microsomes are useful in vitro models of hepatic clearance. The human or mouse microsomes were incubated with the test compounds at 37° C. in the presence of the co-factor, NADPH, which initiated the reaction. The reaction was terminated by the addition of methanol. Following centrifugation, the supernatant was analyzed on the LC-MS/MS. The disappearance of test compound was monitored over a 45 minute time period.

Tested compounds included: (3aS,6aR)-3a-(3,4-dichlorophenyl) octahydrocyclopenta[c]pyrrole; (3aR,6aS)-3a-(3,4-dichlorophenyl)octahydrocyclopenta[c]pyrrole; (3aS,6aR)-3a-(3,4-dichlorophenyl)-2-methyloctahydrocyclopenta[c]pyrrole; (3aR,6aS)-3a-(3,4-dichlorophenyl)-2-methyloctahydrocyclopenta[c]pyrrole; (3aS,7aR)-3a-(3,4-dichlorophenyl)octahydro-1H-isoindole; (3aR,7aS)-3a-(3,4-dichlorophenyl)octahydro-1H-isoindole; (3aR,7aS)-3a-(3,4-dichlorophenyl)-2-methyloctahydro-1H-isoindole; (3aS,7aR)-3a-(3,4-dichlorophenyl)-2-methyloctahydro-1H-isoindole; (3aR,7aS)-3a-(3,4-dichlorophenyl)-2-ethyloctahydro-1H-isoindole; and (3aS,7aR)-3a-(3,4-dichlorophenyl)-2-ethyloctahydro-1H-isoindole. The half-lives ranged from 22 to 262 minutes and 8 to 91 minutes in human and mouse liver microsomes, respectively.

6.4 Pain Models

Effects of (3aR,6aS)-3a-(3,4-Dichlorophenyl)octahydrocyclopenta[c]pyrrole on acute and persistent inflammatory pain were evaluated in male rats. Pain was induced experimentally by application of a chemical irritant, formalin, which results in a biphasic behavioral response that includes both early (Phase 1, 0-9 minutes) and late (Phase 2, 10-60 minutes) phase flinching behavior. The early phase response is considered to be the result of C-fiber activation while the late phase appears to be dependent on the combination of an inflammatory response in the tissue and functional changes in the dorsal horn of the spinal cord.

6.4.1 Procedures

Male rats (Sprague-Dawley, 272-315 g, Harlan) were housed 4 animals per cage in a temperature-controlled environment on a 12-hour light-dark cycle with food and water available ad libitum. Animals were allowed to acclimate to the facility for at least 5 days before testing. On the day of the study, a flexible, light-weight, 'C'-shaped metal band was applied to one hind paw and the rat was dosed orally (PO, 3 mL/kg, via gavage) or intraperitoneally (IP, 1 mL/kg) with vehicle (50 mM acetate buffer (pH 4.5)), (3aR,6aS)-3a-(3,4-dichlorophenyl)octahydrocyclopenta[c]pyrrole or gabapentin. (3aR,6aS)-3a-(3,4-Dichlorophenyl) octahydrocyclopenta[c]pyrrole was administered at 3, 10 and 30 mg/kg PO in 50 mM acetate buffer (pH 4.5) vehicle. Gabapentin (AvaChem Scientific) was administered at 100 mg/kg IP in saline vehicle as a positive control. Sixty minutes after compound administration, animals were administered a dilute formalin solution (5%, 50 μL) into the dorsal aspect of the hind paw with the 'C'-shaped metal band and then immediately placed in individual test cylinders (Automated Nociception Analyzer, UCSD, San Diego, Calif.). Formalin-induced flinching behavior was recorded for 60 minutes.

6.4.2 Results

Formalin administration resulted in a biphasic flinch response, in which the sum of behavior was greater in phase II (10-60 minutes post formalin) compared to phase I (0-9 minutes post formalin). (3aR,6aS)-3a-(3,4-Dichlorophenyl) octahydrocyclopenta[c]pyrrole administration resulted in a significant, dose-related decrease in flinching behavior during phases I and II. Gabapentin administration resulted in a significant and selective attenuation of phase II formalin-induced flinching behavior.

Figure 3:
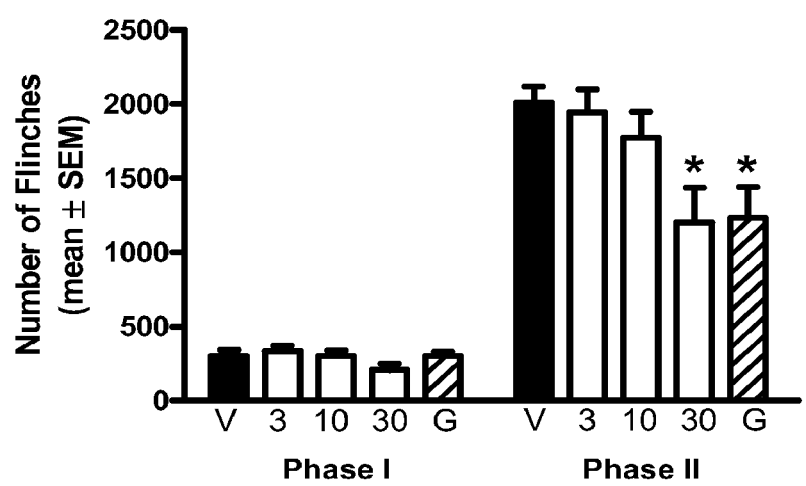
FIG. 3 illustrates the effects of (3aR,6aS)-3a-(3,4-dichlorophenyl) octahydrocyclopenta[c]pyrrole ("the test compound") on flinching responses. (V: Vehicle; 3: 3 mg/kg test compound; 10: 10 mg/kg test compound; 30: 30 mg/kg testcompound; and G: Gabapentine (100 mg/kg)).

As shown in FIG. 3, acute oral administration of (3aR, 6aS)-3a-(3,4-Dichlorophenyl) octahydrocyclopenta[c]pyrrole significantly and dose-dependently attenuated formalin-induced flinching behavior in a non-selective manner when tested in naïve male rats up to 30 mg/kg. The robustness of the assay was confirmed by the significant and selective attenuation of phase II formalin-induced flinching behavior by the positive control, gabapentin. These results indicate that (3aR,6aS)-3a-(3,4-Dichlorophenyl) octahydrocyclopenta[c]pyrrole effectively reduced acute and persistent inflammatory pain in rats and, thus, indicates the compound's potential efficacy in relieving pain.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

All of the patents, patent applications and publications referred to herein are incorporated herein in their entireties. Citation or identification of any reference in this application is not an admission that such reference is available as prior art to this application. The full scope of the disclosure is better understood with reference to the appended claims.

What is claimed is:

1. A pharmaceutical composition, comprising a therapeutically effective amount of a compound selected from the group consisting of:

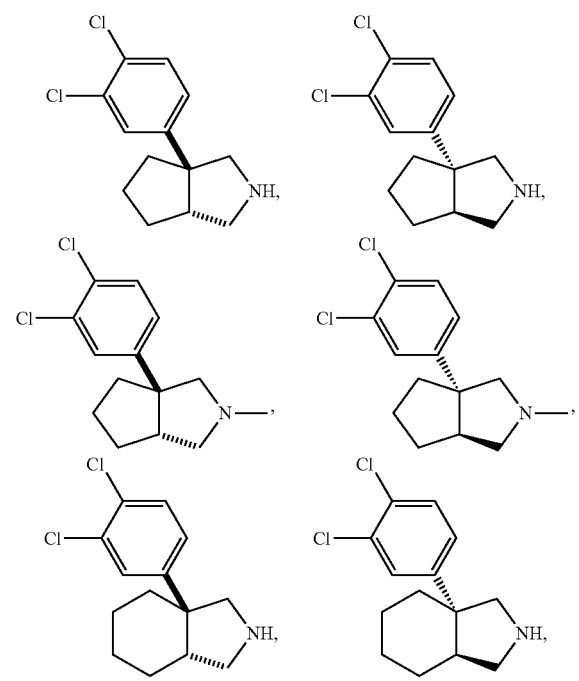

-continued

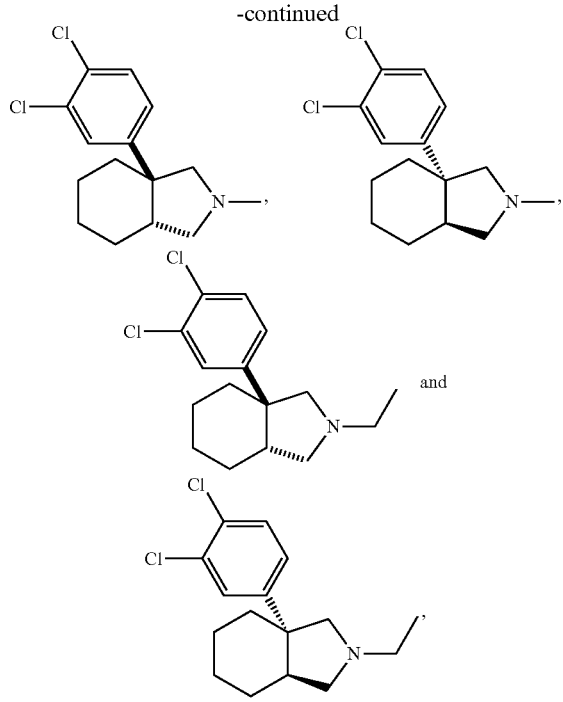

or a pharmaceutically acceptable salt, solvate or stereoisomer thereof, and a pharmaceutically acceptable excipient.

2. The pharmaceutical composition of claim 1, which further comprises one or more additional active agents.

3. A method of treating depression, comprising the step of administering the pharmaceutical composition according to claim 1 to a patient in need thereof.

4. The method of claim 3, wherein the patient is human.

5. A method of treating a central nervous system disorder, comprising the step of administering the pharmaceutical composition according to claim 1 to a patient in need thereof.

6. The method of claim 5, wherein the patient is human.

7. The method of claim 5, wherein said central nervous system disorder is depression, cognitive deficit, fibromyalgia, pain, sleep disorder, attention deficit disorder (ADD), attention deficit hyperactivity disorder (ADHD), restless leg syndrome, schizophrenia, anxiety, obsessive compulsive disorder, posttraumatic stress disorder, premenstrual dysphoria, or a neurodegenerative disease.

8. The method of claim 5, wherein the depression is major depressive disorder (MDD), unipolar depression, bipolar disorder, seasonal affective disorder (SAD) or dysthymia.

9. The method of claim 5, wherein the neurodegenerative disease is Parkinson's disease.

10. The method of claim 5, wherein the sleep disorder is sleep apnea.

11. The method of claim 5, wherein the pain is neuropathic pain.

* * * * *